United States Patent [19]

Sprunt et al.

[11] Patent Number: 4,799,382
[45] Date of Patent: Jan. 24, 1989

[54] METHOD FOR DETERMINING RESERVOIR CHARACTERISTICS OF A POROUS MATERIAL

[75] Inventors: Eve S. Sprunt, Farmers Branch; David P. Yale, Dallas, both of Tex.

[73] Assignee: Mobil Oil Corporation, New York, N.Y.

[21] Appl. No.: 55,980

[22] Filed: Jun. 1, 1987

[51] Int. Cl.$^4$ .................. G01N 15/08; E21B 49/02
[52] U.S. Cl. .......................... 73/153; 73/38; 73/821; 378/4
[58] Field of Search ............ 73/38, 153, 813, 821, 73/825; 378/1, 4, 210

[56] References Cited

U.S. PATENT DOCUMENTS

| | | | |
|---|---|---|---|
| 3,839,899 | 10/1974 | McMillen | 73/38 |
| 4,157,472 | 6/1979 | Beck, Jr. et al. | 250/443 |
| 4,283,629 | 8/1981 | Habermehl et al. | 250/445 |
| 4,399,509 | 8/1983 | Hounsfield | 364/414 |
| 4,422,177 | 12/1983 | Mastronardi et al. | 378/17 |
| 4,562,726 | 1/1986 | Barnaby | 73/38 |
| 4,599,891 | 7/1986 | Brauer et al. | 73/38 |
| 4,627,270 | 12/1986 | Jones | 73/38 |
| 4,649,483 | 3/1987 | Dixon, Jr. | 364/422 |
| 4,688,238 | 8/1987 | Sprunt et al. | 378/4 |
| 4,710,948 | 12/1987 | Withjack | 73/38 |

OTHER PUBLICATIONS

"Petroleum Production Engineering", L. C. Uren, 4th Ed., pp. 660–669.
"API Recommended Practice for Core-Analysis Procedure", *Am. Petroleum Inst.*, Dallas First Edition, 8/60, pp. 2–55.
Reports: "Computed Tomographic Analysis of Meteorite Inclusions", *Science*, vol. 219, Jan. 28, 1983, pp. 383–384.

*Primary Examiner*—Stewart J. Levy
*Assistant Examiner*—Kevin D. O'Shea
*Attorney, Agent, or Firm*—Alexander J. McKillop; Michael G. Gilman; George W. Hager, Jr.

[57] ABSTRACT

Measurements of reservoir characteristics of a core sample of a subsurface formation are carried out with the core sample being subjected to pressure cycling. Pore volume changes during such pressure cycling are measured. Pore compressibility is determined from a plot of the measured pore volume change versus pressure. Scanning of the core sample with X-rays each pressure cycle identifies the pressure at which fracturing is initiated.

11 Claims, 3 Drawing Sheets

METHOD FOR DETERMINING RESERVOIR CHARACTERISTICS OF A POROUS MATERIAL

BACKGROUND OF THE INVENTION

In the production of minerals, e.g., oil and gas, certain reservoir properties of a subterranean reservoir must be determined. Two of the most important of these properties are the porosity and permeability of the reservoir. Porosity of a material is the ratio of the aggregate volume of its void or pore spaces (i.e., pore volume) to its gross bulk volume and, in the case of an oil or gas reservoir, is a measure of the capacity within the reservoir rock which is available for storing oil or gas. Permeability of a material is a measure of the ability of the material to transmit fluids through its pore spaces and is inversely proportional to the flow resistance offered by the material. Another important parameter is pore compressibility, which is change in porosity, or pore and bulk volume, as a function of pressure.

Normally, these parameters are determined by taking core samples from the reservoir and carrying out well-defined measurement techniques on the samples. There are several techniques available for making such measurements, many of which are described in *PETROLEUM PRODUCTION ENGINEERING - DEVELOPMENT* by L. C. Uren, Fourth Edition, McGraw-Hill Book Company, Inc., 1956, pps. 660-669. Another standard reference is American Petroleum Institute, *API Recommended Practice for Core-Analysis Procedure*, API RP 40, 1960, 55 pp.

A more recently applied technique involved computed tomography (CT) technology which has been in use in the medical field for a number of years. CT scanning instruments produce a cross-sectional view through the subject material along any chosen axis. The advantages of CT scanning over conventional radiography is found in its ability to display the electron density variations within the object scanned in a two-dimensional X-ray image. In medical CT scanners, an X-ray source and a detector array circle a patient in a period of about 2 to 9 seconds and produces an image with maximum resolutions of 0.25 mm in the X-Y plane. This plane can be moved in discrete intervals to obtain information in three dimensions. For more details of such medical CT scanners, reference may be made to U.S. Pat. No. 4,157,472 to Beck, Jr. and Barrett (Assignee: General Electric Company) and U.S. Pat. No. 4,399,509 to Hounsfield (Assignee: EMI Limited).

Many other applications of CT scanning can also be made. For example, in an article entitled, "Computed Tomographic Analysis of Meteorite Inclusions", *Science*, pps. 383-384, Jan. 28, 1983, there is described the non-destructing testing of meteorites for isotopic anomalies in calcium- and aluminum-rich inclusions of heterogeneous materials, such as Allende. The CT scanning equipment described in such article is the Deltascan 2020 from Technicare. In a further application, CT scanning has been applied to the non-destructive testing of wood materials, such as for disease in living trees, see U.S. Pat. No. 4,283,629 to Habermehl. In a yet further application, CT scanning has been applied to the examination of non-living objects, such as motors, ingots, pipes, etc., see U.S. Pat. No. 4,422,177 to Mastronardi, et al. (Assignee: American Science and Engineering, Inc.).

More recently, the CT scanning and technology has been applied to the field of energy research for examining the interior of stationary or slowly changing earth materials, such as coal, shale and drilling cores. Processes involved in coal gasification and combustion have been monitored using time-lapse CT imagery to observe changes in density (e.g., thermal expansion, fracturing, emission of gases, consumption by combustion) during progressive heating in a controlled atmosphere. Core flooding experiments can now be carried out with CT scanning to aid in enhanced oil recovery and fluid mobility control. For example, the permeability of materials within core samples to various fluids at varying conditions of temperature and pressure can be determined. Such experiments might involve flushing a fluid through a core sample and monitoring the shape of the fluid fronts. By subtracting the images of the cores before and after flooding, the exact shapes of the fluid front was determined. Such core flood experiments allows the interior of the core sample to be observed without disturbing the sample. The sweep efficiency and flow paths of fluids of interest may now be studied on the scale of millimeters. The penetration of X-rays allows experiments to be performed with up to 4-inch diameter core samples.

Drilling fluids can be analyzed by CT scanning as such fluids are characterized by high-density brines, various organics and several compositionally different weighting agents. Formation damage can be investigated since CT scanning can detect migration of clays, absorption of organics and the reversibility of completion fluid penetration. Shale oil recovery can be aided as CT scanning could detect penetration by solvents and could directly measure structure changes on retorting.

U.S. Pat. No. 4,649,483 to Dixon discloses a method for determining fluid saturation in a porous media through the use of CT scanning. Multi-phase fluid saturation in a sample of a porous media is determined through computer tomographic scanning. The sample is scanned with X-rays of differing energies in both the fluid saturated and fluid-extracted states. Each of the extracted fluids is also scanned at differing X-ray energies. The computed tomographic images produced are utilized in the determination of the X-ray mass attenuation coefficients for the sample and the extracted fluids. From these mass attenuation coefficients, the weight fractions and volume fractions of each of the extracted fluids are determined.

U.S. Pat. No. 4,688,238 issued Aug. 18, 1987, to Sprunt et al. discloses a method for using CT scanning over a range of confining pressures on a core sample to determine pore volume change, pore compressibility and core fracturing. A core sample with a surrounding elastic jacket is placed in a confining pressure cell. Pressure is applied to the cell to press the jacket into contact with the surface of the sample. The pressure in the cell is increased stepwise over a plurality of pressure points. The sample is scanned at a plurality of locations with X-rays at each of the pressure points. Computed tomographic images of the sample are produced for each of the X-ray scans. The conformance of the jacket to the sample is determined from these computed tomographic images. From such conformance, a range of confining pressures is determined over which pore volume and pore compressibility of the sample are measured without being affected by improper conformance of the jacket to the surface of the sample. Also rock fracturing is determined from the pressure at which crushing of the sample destroys permeable channels within the sample and results in a permeability measurement that is lower than the actual permeability of the sample.

SUMMARY OF THE INVENTION

The present invention is directed to a method for measuring reservoir characteristics of a core sample from a subsurface formation by subjecting the core sample to pressure cycling. Pore volume changes during such pressure cycling are measured. Pore compressibility is determined from a plot of the measured pore volume change versus pressure. Scanning of the core sample with X-rays each pressure cycle identifies the pressure at which fracture is initiated.

More particularly, a core sample from a subsurface formation is surrounded with an elastic jacket and is placed in a confining pressure cell. Pressure within the cell is cycled between a base pressure that is sufficient to reduce any cavity between the core sample and the elastic jacket and a plurality of successively increasing maximum pressures. The pore volume change between the base pressure and the maximum pressure is measured for a plurality of points along each pressure cycle. These measured pore volume changes are plotted against pressure to provide an indication of pore compressibility.

In a further aspect, the core sample is scanned with X-rays at least once for each pressure cycle and a computed tomographic image is produced. From the plurality of produced images, a determination is made of the pressure at which fracturing initiates and of the location or locations within the sample at which fracturing occurs. Preferably, at the end of each pressure cycle, the pressure on the core sample is reduced to ambient from the base pressure and the core sample is removed from the confining pressure cell before the core sample is scanned with X-rays. Fractures can be more readily identified when the pressure on the core sample is ambient and the produced images will have better resolution when the scanning X-rays do not have to pass through the wall of the confining pressure cell.

In another aspect, the core sample is scanned with X-rays to produce a computed tomographic image prior to any pressure cycling to determine the position and morphology of existing pore spaces and existing fractures.

DESCRIPTION OF THE PREFERRED EMBODIMENT

The present invention is an improvement over the method for measuring core sample reservoir characteristics disclosed in U.S. Pat. No. 4,688,238. In the present invention, pressure cycling with increasing maximum pressure is employed. This is an important distinction over such patent since fractures occurring at elevated pressures may remain closed at such pressures and may not be detectable by the teachings of such patent. Also pressure cycling nullifies jacket intrusion effects on pore compressibility measurements of the core sample. This pressure cycling and accompanying measurements will be described more fully following a brief description of the system utilized to carryout the method of the invention.

Figure 1:
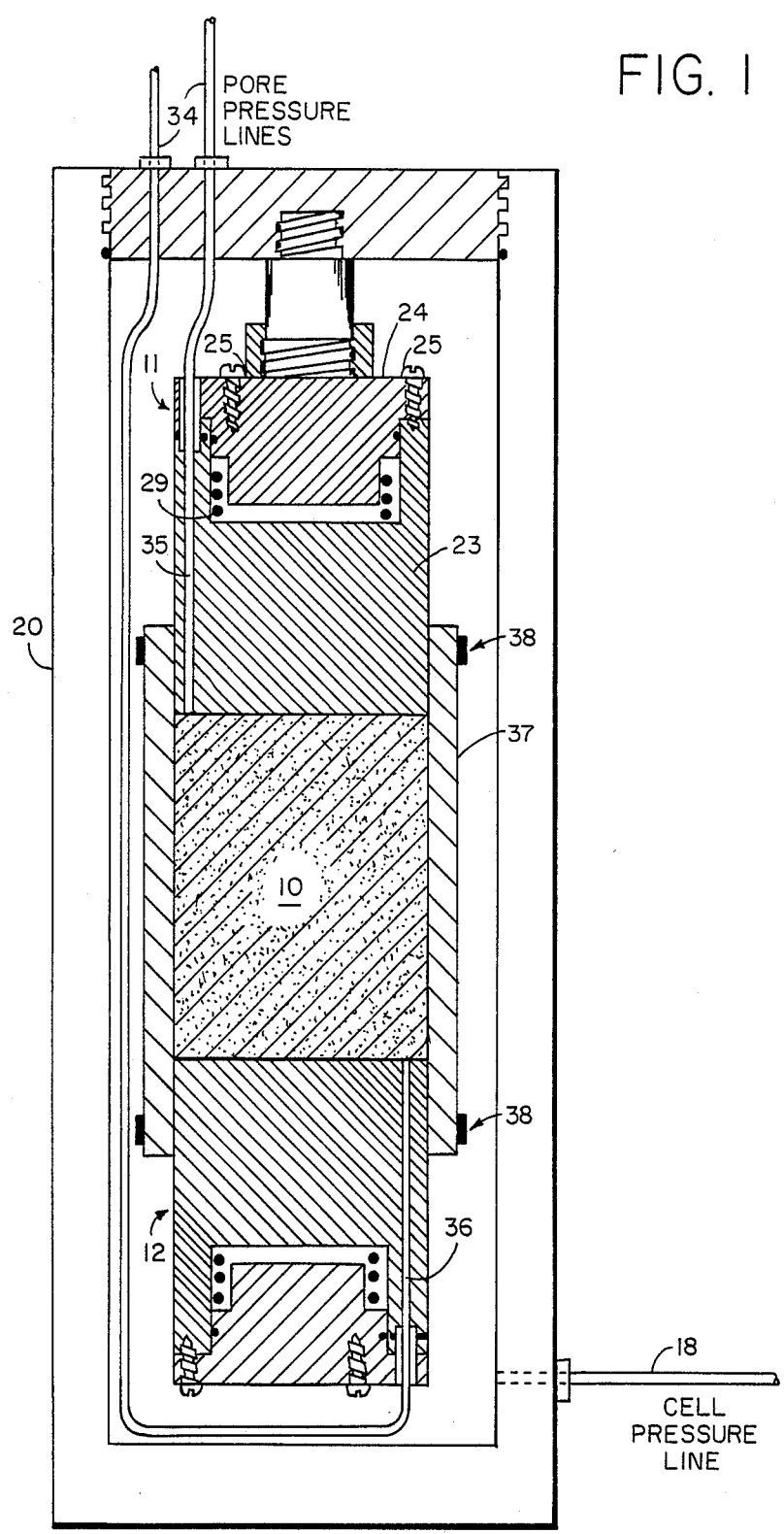
FIG. 1 is a cross-sectional view of a confining pressure cell housing a sample of porous material to be examined in accordance with the method of the present invention.

Referring first to FIG. 1, a sample 10 of a porous material, such as a core sample of a subterranean earth formation, to be examined in accordance with the pressure cycling method of the present invention is mounted between a housing 11 and a housing 12 and is enclosed within a confining pressure cell 20 for subjecting the core sample to varying pressure conditions. The confining pressure condition within the cell 20 is established by the cell pressure line 18. Housing 11 comprises an annular member 23 and a cover member 24. Such cover member 24 encloses the open end of the annular member 23 and is secured by screws 25. The face of the member 23 is maintained in good contact with the core sample 10 through spring-loading provided by one or more spring-like members 29. Pore pressure lines 34 provide the desired fluid pressure to the core sample 10 by way of the passageways 35 and 36 in the housings 11 and 12, respectively.

Figure 2:
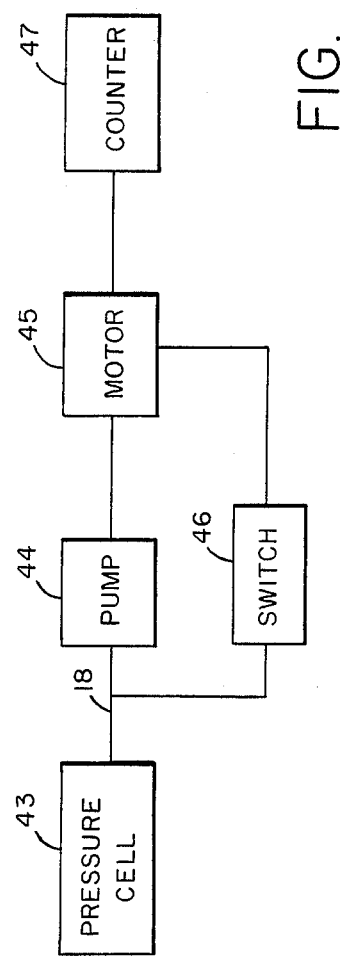
FIG. 2 is a block diagram of the system for supplying confining pressure to the pressure cell of FIG. 1.

The core sample 10 and portions of housings 11 and 12 are surrounded by a jacket, or sleeve, 37 which may be made of an impermeable elastic material, such as rubber, for example. The jacket 37 is secured to the housings 11 and 12 and the core sample 10 by the clamps 38. The confining pressure applied to cell 20 through cell pressure line 18 is supplied by the system illustrated in FIG. 2. Line 18 is connected to pump means 44 which is operated by motor 45. Pump means 44 is of the type which allows accurate measurement of the amount of fluid pumped, e.g., a screw-feed, positive-displacement pump which has a capacity forward of its displacement piston sufficient to store the volume of non-compressible fluid necessary for use in the present invention. This negates the need for the separate fluid reservoir as is well understood by those skilled in the art, although such a reservoir could be easily provided. Motor 45 is preferably of the type commonly referred to as a stepping motor so that it moves pump means 44 in discrete increments to force non-compressible fluid through pressure supply line 18 into cell 20 to expand jacket 37 into contact with core sample 10. The pressure within the cell 20 may be varied over a plurality of pressure points. A counter 47 records the number of steps of motor 45. Pressure-sensitive switch 46 is connected into pressure supply line 18 to shut off motor 45 when a preset pressure has been reached. By counting the number of steps of motor 45 and knowing the corresponding displacement of pump 44 for each step, the exact amount of fluid which is necessary to reach the preset pressure can be determined.

The pressure cycling of the present invention for determining lithology utilizing the system described above in conjunction with FIGS. 1 and 2 will now be set forth in detail.

The sample 10 may initially be measured for porosity and permeability by conventional methods prior to being subjected to pressure cycling. Core sample 10 should have as large a diameter as possible, preferably the full diameter of the recovered core. In too small diameter cores it is difficult to distinguish between crushing due to jacket intrusion and crushing due to failure of the rock material itself. After mounting the sample 10 inside the jacket 37, a more rigid layer such as metal, for example, may be wrapped around the sample to reduce intrusion of the jacket into the sample.

The sample 10 is now ready to be placed in the confining pressure cell 20. Initially the confining pressure is raised to some base pressure 500 psi, for example, from which all subsequent measurements are referred to. This base pressure is used as a baseline from which pore volume changes can be measured. This pressure should be high enough to eliminate most of the cavity between the surface of the sample 10 and the surrounding jacket 37. From this initial base pressure, the sample 10 is subjected to a pressure cycling in which maximum confining pressure is increased each cycle over that of the previous cycle and is returned to either the base pressure or ambient between each cycle.

More particularly, after the confining pressure has stabilized at the base pressure an initial pore volume measurement is made. The first pressure cycle is then initiated with the pressure cycling to a first maximum pressure before returning to the base pressure. The pressure is allowed to stabilize at the maximum pressure for the first pressure cycle, such stabilization may take one hour or longer. After stabilization a pore volume measurement is made to determine the pore compressibility from the base pressure to the maximum pressure for this first cycle. Following this pore volume measurement at the first cycle maximum pressure point the confining pressure is reduced at least back to the base pressure. After stabilization at the base pressure subsequent pressure cycles are initiated with accompanying pore volume measurements. The maximum pressure for each subsequent pressure cycle increases over that of the previous pressure cycle. This pressure cycling may be continued for any number of cycles until core crushing occurs.

Figure 3:
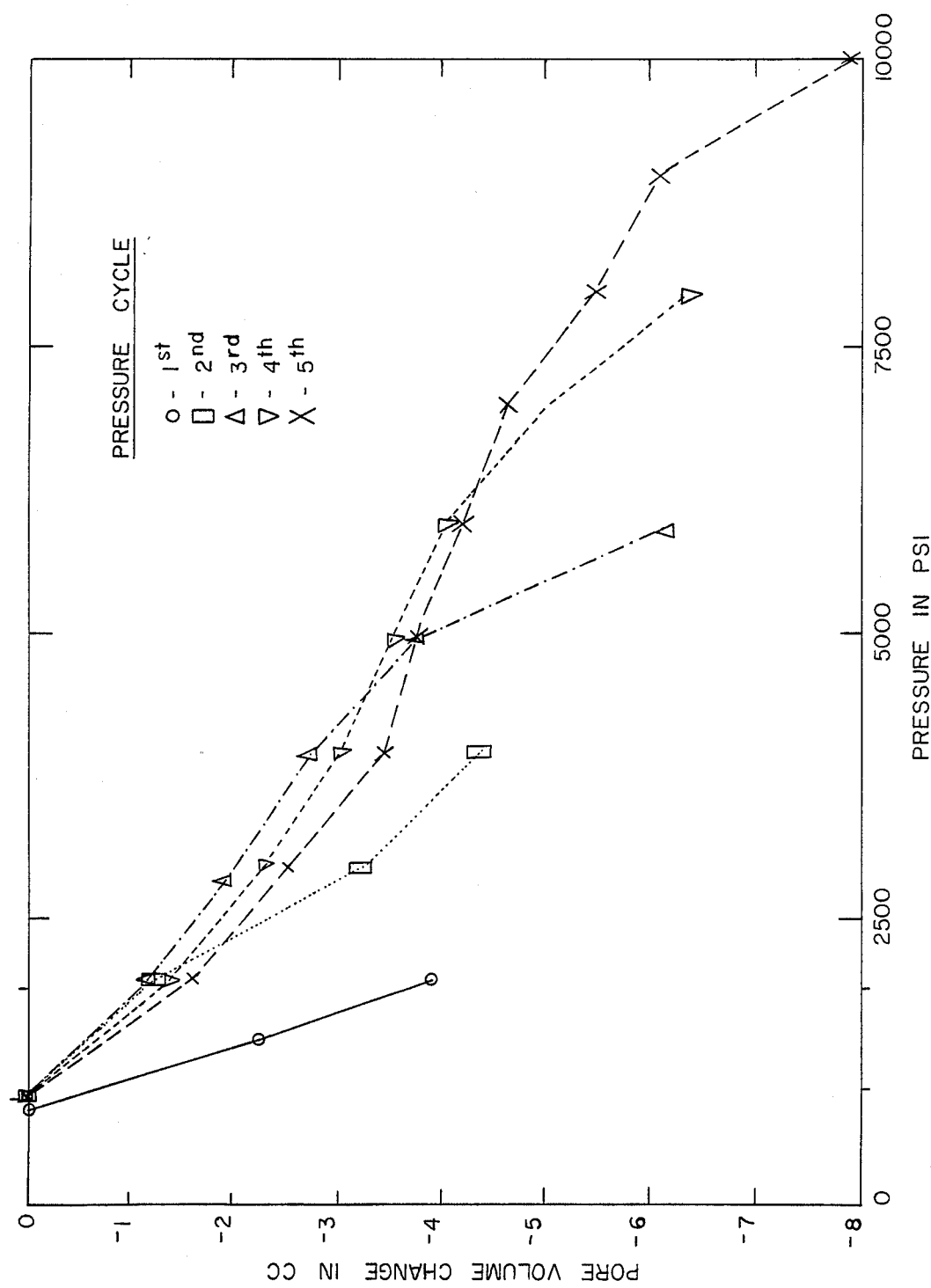
FIG. 3 is a plot of pore volume data obtained.

An example of the pore volume data acquired on one core sample taken from a subsurface formation in the Arun field is shown in FIG. 3. A series of pressure cycles were run. The base pressure was set at 500 psi. The maximum pressure point for the first cycle was 1000 psi. Five subsequent cycles were carried out with the maximum pressure increasing to 2000, 4000, 6000, 8000 and 10,000 psi respectively. It can also be noted from FIG. 3 that pore volume measurements were made at every 1000 psi point during each pressure cycle. For more details as to pore volume measurements on core samples reference may be made to U.S. Pat. No. 3,839,899 to McMillen, the teaching of which is incorporated by reference. This pressure cycling nullifies the jacket intrusion effects on pore compressibility of the core sample. The change in pore volume due to pressure in the absence of jacket intrusion can be observed in the pressure overlap between any pressure cycle and immediately the preceding pressure cycle. If the core sample crushes at a pressure or pressures with the pressuring cycling range, that pressure can be determined from pore compressibility curves. The pore compressibility can be determined directly from the overlapping portion of the pore volume change versus pressure curves of FIG. 3, For example, Table 1 gives the compressibility determined from all the pressure points of all the pressure cycles. Table 2 summarizes the data in Table 1 so that comparisons may be made between pressure cycles. The composite value given in Table 2 gives the pore compressibility values determined from the overlapping portions of the pressure cycles.

TABLE 1

Pore Volume 137.9 cc

| Effective Pressure (psi) | Confining Pressure (psi) | Pore Pressure (psi) | Pore Volume Change (cc) | Compressibility ($\times 10^{-6}$ psi$^{-1}$) |
|---|---|---|---|---|
| Cycle 1: | | | | |
| 196 | 2194 | 1998 | * | |
| 494 | 2498 | 2004 | −4.12 | 100.14 |
| 764 | 2764 | 2000 | −6.33 | 59.55 |
| 982 | 2982 | 2000 | −7.80 | 48.69 |
| 1490 | 3490 | 2000 | −10.03 | 31.93 |
| 2000 | 4000 | 2000 | −11.67 | 23.29 |
| Cycle 2: | | | | |
| 184 | 2184 | 2000 | * | |
| 516 | 2518 | 2002 | −2.12 | 46.32 |
| 996 | 2996 | 2000 | −3.28 | 12.40 |
| 1990 | 3990 | 2000 | −4.51 | 8.98 |
| 2986 | 2010 | 2010 | −6.49 | 14.39 |
| 3998 | 5998 | 2000 | −7.63 | 8.16 |
| Cycle 3: | | | | |
| 188 | 2194 | 2006 | * | |
| 488 | 2490 | 2002 | −2.03 | 49.15 |
| 1000 | 3002 | 2002 | −3.36 | 18.75 |
| 1998 | 3998 | 2000 | −4.54 | 8.58 |
| 2982 | 4982 | 2000 | −5.28 | 5.45 |
| 3994 | 5996 | 2002 | −6.06 | 5.60 |
| 5000 | 7000 | 2000 | −7.02 | 6.91 |
| 5904 | 7904 | 2000 | −9.46 | 19.62 |
| Cycle 4: | | | | |
| 200 | 2202 | 2002 | * | |
| 992 | 2994 | 2002 | −4.24 | 38.87 |
| 1988 | 3992 | 2004 | −5.64 | 10.17 |
| 3006 | 5006 | 2000 | −6.51 | 6.16 |
| 4002 | 6002 | 2000 | −7.20 | 5.02 |
| 4990 | 6992 | 2002 | −7.66 | 3.40 |
| 5990 | 7990 | 2000 | −8.23 | 4.12 |
| 6990 | 8990 | 2000 | −9.25 | 7.40 |
| 7992 | 9992 | 2000 | −10.52 | 9.17 |
| Cycle 5: | | | | |
| 205 | 2205 | 2000 | * | |
| 986 | 2990 | 2004 | −5.71 | 53.04 |
| 2000 | 4000 | 2000 | −7.30 | 13.88 |
| 2995 | 4995 | 2000 | −8.25 | 6.87 |
| 4000 | 6000 | 2000 | −9.10 | 6.15 |
| 5008 | 7010 | 2002 | −9.42 | 2.27 |
| 6000 | 6000 | 2000 | −9.87 | 3.29 |
| 7005 | 9005 | 2000 | −10.32 | 3.24 |
| 8000 | 10000 | 2000 | −11.13 | 5.96 |
| 9010 | 11010 | 2000 | −11.74 | 4.38 |
| 9995 | 11995 | 2000 | −13.56 | 13.41 |

*Reference pressure from which changes in pore volume are measured.

TABLE 2

| Approximate Effective Pressure (psi) | Comparison of Compressibility From Different Cycles | | | | | |
|---|---|---|---|---|---|---|
| | Compressibility ($\times 10^{-6}$ psi$^{-1}$) | | | | | |
| | Pressure Cycle Number | | | | | Composite Value |
| | 1 | 2 | 3 | 4 | 5 | |
| 500 | 100* | 46* | 49* | | | 46* |
| 1000 | 49 | 12 | 19 | 39* | 53* | 12 |
| 2000 | 23 | 9 | 9 | 10 | 14 | 9 |
| 3000 | | 14 | 5 | 6 | 7 | 5 |
| 4000 | | 8 | 6 | 5 | 6 | 6 |
| 5000 | | | 7 | 3 | 2 | 3 |
| 6000 | | | 20 | 4 | 3 | 4 |
| 7000 | | | | 7 | 3 | 3 |
| 8000 | | | | 9 | 6 | 6 |
| 9000 | | | | | 4 | NA |
| 10000 | | | | | 13 | NA |

*The first compressibility value of any cycle is dominated by reseating of the sample jacket. Also, the pressure step over which the compressibility value is determined will influence the value if the flat portion of the compressibility versus pressure curve has not been reached.
NA: Value not available because there was no overlapping pressure cycle.

One of the specific features of the present invention is the enhanced detection of core sample fracturing. At the elevated confining pressures any fractures that occur will be difficult to detect since the fractures will probably be closed. Consequently by cycling the pressure between increasingly higher confining pressures and at least the baseline pressure, the occurrence and location of a fracture can be more readily detected when the pressure is reduced immediately following the fracture. At reduced pressure the fracture will open and be more readily detectable. CT scanning of the core sample is carried out at a number of pressure points during the pressure cycle. However, CT scanning at the initial base pressure and subsequent base pressure points will enhance fracture determination over CT scanning at intermediate and maximum pressure points. CT scanning at such base pressure points will be degraded by the confining pressure cell 20 in which the core sample is mounted. Since the X-rays of the CT scan must pass through this cell the CT scan resolution will be reduced by the thickness of the pressure cell wall. In view of this, the confining pressure on the core sample is reduced below base pressure to ambient following each pressure cycle and the core sample is removed from the confining pressure cell for CT scanning. Following CT scanning at ambient conditions, the core sample is replaced in the confining pressure cell in preparation for the subsequent pressure cycle.

Figure 4:
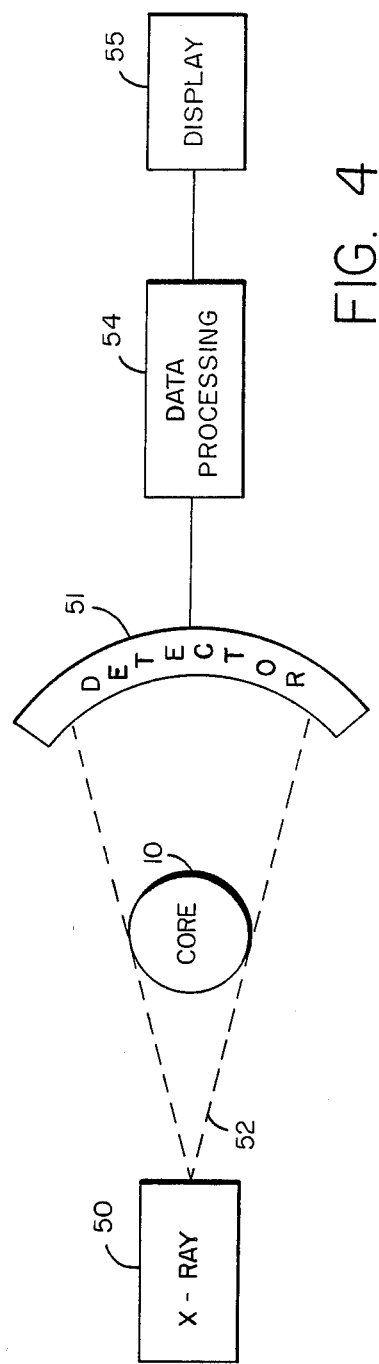
FIG. 4 is a pictorial view of a CT scanning system for use in scanning a core of porous material with X-rays in accordance with the method of the present invention.

A system for the CT scanning of a core sample is described in detail in the aforementioned U.S. patent application Ser. No. 868,487, now U.S. Pat. No. 4,688,238. Briefly however, such a system is shown in FIG. 4 wherein X-ray energy provided by the X-ray tube 50 passes through the core sample 10 and falls on the detector array 51. Rotation of the core sample within the X-ray fan beam 52 is provided by a gantry (not shown). In an alternative embodiment, the core sample 10 may remain stationary and the gantry may be used to rotate the X-ray tube 50 and detector 51 about the core sample. In medical applications, CT scanning rates are usually in the order of 2 to 9 seconds. However, patient dose limitations are of no concern in the present application, and scan times of the core sample can be up to 1 minute per scan, or even longer, if desired. The output of the detector array 51 is passed through the data processing unit 54 to the display unit 55. After a desired number of scans are completed for a core sample slice, the sample is indexed one slice-width through the X-ray fan beam to place the next adjacent sample slice within the path of the X-ray fan beam. In this manner, a 3-D tomographic presentation is made on the display unit 55 of the entire sample by compositing the cross-sectional view of each of the scan slices. Such a CT scanning system, while not forming a part of the present invention, is used in accordance with the pressure cycling method of the present invention to determine the conformance of the jacket 37 to the surface of the core sample 10 under varying pressure conditions and to determine core sample 10 fracturing.

For a more detailed description of CT scanning systems which may be utilized in the method of the present invention, reference may be made to each of the aforementioned U.S. patents and the referenced *Science* article, the teachings of which are incorporated herein by reference. A particularly suitable detector array 51 for use in the present invention for a 100 micron resolution would comprise a 1024×1 linear array of photodiodes on a 0.001 inch center-to-center spacing with pixel (picture element) aperatures of 0.001 inch by 0.1 inch. An example of such an array is the Reticon 1024S/fiber optic faceplate. For a lower 250 micro resolution, a 200×1 linear array of photodiodes on a 0.01 inch center-to-center spacing with pixel aperatures of 0.01 inch to 0.1 inch would be suitable. An example of such an array is that used in digital mammography equipment supplied by Bio-Imaging Research, Inc. Optically coupled to the input surfaces of the photodiode arrays are scintillation arrays comprised of a plurality of discrete scintillators having X-ray sensitive fluorescent materials individually and optically coupled to the input surfaces of the discrete photodiodes. Such materials may comprise $CdWO_4$, $C_5I$, $GdOBr$ or $LaOBr$, among others. Such combination of scintillators and photodiodes provides for a complete scintillation counter. The photodiodes provide electrical signals whose heights are proportional to the X-ray energy falling upon the surfaces of the scintillators. After suitable amplification, the signals are digitized for use in producing a desired tomographic display.

While preferred embodiments of the present invention have been described, numerous modifications and alterations may be made without departing from the spirit and scope of the invention as set forth in the appended claims.

What is claimed is:

1. A method for determining a measurement of reservoir characteristics of a core sample of a subsurface formation, comprising the steps of:
   (a) surrounding said core sample with an elastic jacket,
   (b) placing said sample in a confining pressure cell,
   (c) cycling the pressure within the cell between a base pressure that is sufficient to reduce any cavity between said core sample and said elastic jacket and a plurality of successively increasing maximum pressures, and
   (d) measuring the pore volume change between the base pressure and the maximum pressure for each pressure cycle.

2. The method of claim 1 further comprising the measuring of the pore volume change between the base pressure and a plurality of pressure points between said base pressure and the maximum pressure point for each pressure cycle.

3. The method of claim 2 further comprising the step of determining pore compressibility from a plot of pore volume change versus pressure for each pressure cycle.

4. The method of claim 1 further comprising the steps of:
   (a) scanning said core sample with X-rays at least once for each pressure cycle,
   (b) producing computed tomographic images of said sample for each of said pressure cycles, and
   (c) determining core sample from said computed tomographic images.

5. The method of claim 4 wherein the determination of core sample fracturing includes the determination of the pressure cycle during which fracturing of said core sample is initiated.

6. The method of claim 4 wherein the determination of core sample fracturing includes the determination of the location or locations within said core sample at which fracturing occurs.

7. The method of claim 1 wherein said core sample is scanned with X-rays to produce a computed tomographic image prior to any pressure cycling to determine the position and morphology of existing pore spaces and of existing fractures.

8. A method for determining a measurement of reservoir characteristics of a core sample of a subsurface formation, comprising the steps of:
   (a) surrounding said core sample with an elastic jacket,
   (b) placing said sample in a confining pressure cell,
   (c) cycling the pressure within the cell between ambient pressure and a plurality of successively increasing maximum pressures,
   (d) scanning said core sample with X-rays at ambient pressure following each pressure cycle,
   (e) producing computed tomographic images of said sample at ambient pressure following each pressure cycle, and
   (f) determining core sample fracturing from said computed tomographic images.

9. The method of claim 8 wherein the determination of core sample fracturing includes the determination of the pressure cycle during which fracture of said core sample is initiated.

10. The method of claim 8 wherein the determination of core sample fracturing includes the determination of the location or locations within said core sample at which fracturing occurs.

11. The method of claim 8 wherein said core sample is removed from said confining pressure cell for the scanning of said sample with X-rays and is thereafter replaced within said confining pressure cell for the next pressure cycle.

* * * * *